(12) United States Patent
Sherman

(10) Patent No.: US 6,340,698 B1
(45) Date of Patent: Jan. 22, 2002

(54) ANTIFUNGAL SOLUTIONS

(75) Inventor: Bernard Charles Sherman, 50 Old Colony Road, Willowdale, ON (CA), M2L 2K1

(73) Assignee: Bernard Charles Sherman, Willowdale (CA)

(*) Notice: Subject to any disclaimer, the term of this patent is extended or adjusted under 35 U.S.C. 154(b) by 0 days.

(21) Appl. No.: 09/718,514

(22) Filed: Nov. 24, 2000

(30) Foreign Application Priority Data

Nov. 26, 1999 (CA) .............................................. 2291346

(51) Int. Cl.[7] ............................................. A61K 31/415
(52) U.S. Cl. ...................................................... 514/400
(58) Field of Search .......................................... 514/400

(56) References Cited

U.S. PATENT DOCUMENTS

| | | | |
|---|---|---|---|
| 4,727,064 A | | 2/1988 | Pitha ............................ 514/58 |
| 5,707,975 A | | 1/1998 | Francois et al. ............... 514/58 |
| 5,750,147 A | * | 5/1998 | Kantor ....................... 424/491 |
| 6,100,285 A | * | 8/2000 | Kantor ....................... 514/400 |
| 6,143,794 A | * | 11/2000 | Chaudhuri et al. ......... 514/655 |

* cited by examiner

*Primary Examiner*—James H. Reamer
(74) *Attorney, Agent, or Firm*—Neil H. Hughes; Ivor M. Hughes; Marcelo K. Sarkis

(57) ABSTRACT

A solution for oral administration comprising intraconazole or saperconazole, an acid, an alcoholic co-solvent.

20 Claims, No Drawings

ANTIFUNGAL SOLUTIONS

BACKGROUND OF THE INVENTION

Itraconazole and saperconazole are compounds useful for treating fungal infections in mammals. They may be administered topically, parenterally or orally.

Itraconazole and saperconazole are both particularly insoluble in water. This makes it difficult to formulate itraconazole or saperconazole into aqueous solutions, particularly solutions that are suitable for oral administration.

A solution for oral administration comprising itraconazole is sold in the United States and elsewhere under the tradename Sporanox®. The strength of the solution is 10 mg itraconazole per mL, and the inactive ingredients in addition to water are hydroxypropyl-β-cyclodextrin, propylene glycol, sorbitol hydrochloric acid, sodium hydroxide, sodium saccharin, and flavours.

The purpose of the hydroxypropyl-β-cyclodextrin is to improve the aqueous solubility of itraconazole by forming an inclusion complex. This use of cyclodextrin derivatives for solubilizing drugs such as itraconazole and saperconazole is disclosed in U.S. Pat. Nos. 4,727,064 and 5,707,975.

While the use of cyclodextrin derivatives enables production of an oral solution comprising itraconazole or saperconazole, the need to use a cyclodextrin derivative increases the complexity of manufacture of the oral solution and also the cost.

The object of the present invention is thus to enable an oral solution comprising itraconazole or saperconazole, without the use of acyclodextrin derivative to complex the itraconazole or saperconazole.

DESCRIPTION OF THE INVENTION

In this specification and claims, "free itraconazole" and "free saperconazole" will be understood to mean itraconazole and saperconazole not solubilized by complexation with a cyclodextrin derivative.

Although itraconazole and saperconazole are practically insoluble in water, they are soluble in strong acids.

For example, 1 g of free itraconazole can be dissolved in about 3 g of glacial acetic acid or about 3 to 4 g of concentrated hydrochloric acid (i.e. 36–38% HCl in water).

However, strongly acidic solutions are unsuitable for oral administration, and if a solution of itraconazole or saperconazole in strong acid is diluted with water to weaken the acid, the itraconazole or saperconazole precipitates.

It has been found that this problem can be overcome (i.e. the precipitation prevented) by diluting the solution with an alcoholic co-solvent, instead of or in addition to water. Preferred alcoholic co-solvents are propylene glycol, ethanol and glycerol. Most preferred is propylene glycol.

Compositions within the scope of the present invention will thus be solutions in which free itraconazole or free saperconazole is dissolved in a solvent system comprising an acid, and an alcoholic co-solvent. The solvent system will preferably also comprise water. The alcoholic co-solvent will preferably be selected from propylene glycol, ethanol and glycerol, and will most preferably be propylene glycol. It will be understood that a mixture of two or more alcoholic co-solvents may be used instead of one alone.

The concentration of the itraconazole or saperconazole in the solution will preferably be about 10 mg per mL.

The acid will preferably be selected from hydrochloric acid, sulfuric acid and acetic acid, and will most preferably be hydrochloric acid.

The concentration of the alcoholic co-solvent in the solution will be preferably from about 100 to about 800 mg per mL, more preferably from about 200 to about 700 mg per mL, even more preferably from about 300 to about 600 mg per mL, and most preferably from about 400 to about 500 mg per mL.

The pH of solution will be preferably from about 1 to about 4, more preferably from about 1 to about 3, and most preferably from about 1 to about 2.

The solution will optionally contain ingredients in addition to the itraconazole or saperconazole, acid, alcoholic co-solvent, and water.

For example, the solution will preferably contain either sorbitol or sucrose as a sweetener and thickener.

The solution may also contain an artificial sweetener such as, for example, saccharin or saccharin sodium.

The solution will preferably also contain one or more flavouring ingredients, such as, for example, cherry flavour.

The invention will be further understood from the following example, which is intended to be illustrative and not limiting of the invention.

EXAMPLE 1

A solution was prepared comprising ingredients in the following proportions:

| | |
|---|---|
| Itraconazole | 10 mg |
| Concentrated hydrochloric acid | 4 mg |
| Propylene glycol | 520 mg |
| Sorbitol solution 70% | 660 mg |
| Saccharin sodium | 1 mg |
| Artificial flavour | 5 mg |
| | 1180 mg |

Concentrated hydrochloric acid will be understood to mean 36.5–38% HCl in water.

Sorbitol solution 70% is approximately 70% sorbitol and 30% water by weight.

The procedure of manufacture was to dissolve the itraconazole in a mixture of the concentrated hydrochloric acid and propylene glycol, and to then add the remaining ingredients and mix.

The density of the solution was about 1180 mg per mL or 1180 g per L, so that the quantities shown are for 1 L of solution. The pH of this solution was about 1.5.

What is claimed is:

1. A pharmaceutical solution substantially free of cyclodextrin for oral administration comprising itraconazole or saperconazole, an acid, and one or more alcoholic co-solvents, wherein the concentration of alcoholic co-solvent is from greater than about 200 to about 800 mg per mL.

2. The solution of claim 1 comprising as alcoholic co-solvent one or more ingredients selected from propylene glycol, ethanol and glycerol.

3. The solution of claim 2 comprising propylene glycol.

4. The solution of claim 2 further comprising water.

5. The solution of claim 1 or 2, wherein the concentration of itraconazole or saperconazole is about 1 mg per mL.

6. The solution of claim 1, wherein the acid is selected from hydrochloric acid, acetic acid and sulfuric acid.

7. The solution of claim 2, wherein the acid is selected from hydrochloric acid, acetic acid and sulfuric acid.

8. The solution of claim 6, wherein the acid is hydrochloric acid.

9. The solution of claim 1,2,4,6, or 7, wherein the concentration of alcholic co-solvent is from greater than about 200 to about 700 mg per mL.

10. The solution of claim 9, wherein the concentration of alcholic co-solvent is from about 300 to about 600 mg per mL.

11. The solution of claim 10, wherein the concentration of alcoholic co-solvent is from about 400 to about 500 mg per mL.

12. The solution of claim 1,2,4,6 or 7 having a pH of from about 1.0 to about 4.0.

13. The solution of claim 1,2,4,6 or 7 having a pH of from about 1.0 to about 3.0.

14. The solution of claim 1,2,4,6 or 7 having a pH of from about 1.0 to about 2.0.

15. The solution of claim 1,2,4,6 or 7 further comprising sucrose or sorbitol.

16. The solution of claim 15 further comprising sorbitol.

17. The solution of claim 1,2,4,6 or 7 further comprising any artificial sweetener.

18. The solution of claim 17, wherein the artificial sweetener is saccharin or saccharin sodium.

19. The solution of claim 1,2,4,6 or 7 comprising free itraconazole.

20. The solution of claim 1,2,4,6 or 7 comprising free saperconazole.

\* \* \* \* \*